United States Patent [19]

Sasaki et al.

[11] Patent Number: 4,754,045

[45] Date of Patent: Jun. 28, 1988

[54] METHOD FOR PRODUCING HYDROXYPHENYLPROPIONIC ACID ESTER

[75] Inventors: Manji Sasaki, Ibaraki; Chinehito Ebina, Minoo; Haruki Okamura, Osaka; Shinichi Yachigo, Toyonaka; Tamaki Ishii, Suita, all of Japan

[73] Assignee: Sumitomo Chemical Company, Limited, Osaka, Japan

[21] Appl. No.: 868,100

[22] Filed: May 29, 1986

[30] Foreign Application Priority Data

Jun. 13, 1985 [JP] Japan ................... 60-128828

[51] Int. Cl.$^4$ ............... C07D 319/00; C07D 493/10
[52] U.S. Cl. ..................................... 549/335
[58] Field of Search ................... 549/343, 335

[56] References Cited

U.S. PATENT DOCUMENTS 4,576,734  3/1986  Ishii et al. .................. 252/404

FOREIGN PATENT DOCUMENTS 25826   2/1984  Japan.
231089 12/1984  Japan.

OTHER PUBLICATIONS

Ishii et al., Chem. Abstract, 104, 69709w (1986).

*Primary Examiner*—Nicky Chan
*Attorney, Agent, or Firm*—Wenderoth, Lind & Ponack

[57] ABSTRACT

Method for producing 3,9-bis{2-[3-(3-tert-butyl-4-hydroxy-5-methylphenyl)propionyloxy]-1,1-dimethylethyl}-2,4,8,10-tetraoxaspiro[5.5]undecane by ester exchange of a 3-(3-tert-butyl-4-hydroxy-5-methylphenyl)-propionic acid ester with 3,9-bis(2-hydroxy-1,1-dimethylethyl)-2,4,8,10-tetraoxaspiro[5.5]-undecane at a temperature of 170°–250° C. using a calcium compound as a catalyst in an amount of 0.05–1.5 moles per mole of the 3,9-bis(2-hydroxy-1,1-dimethylethyl)-2,4,8,10-tetraoxaspiro[5.5]-undecane.

4 Claims, No Drawings

METHOD FOR PRODUCING HYDROXYPHENYLPROPIONIC ACID ESTER

The present invention relates to a novel method for producing 3,9-bis{2-[3-(3-tert-butyl-4-hydroxy-5-methylphenyl)propionyloxy]-1,1-dimethylethyl}-2,4,8,10-tetraoxaspiro[5.5]undecane represented by the structural formula (III) (hereinafter referred to as "hydroxyphenylpropionic acid ester"),

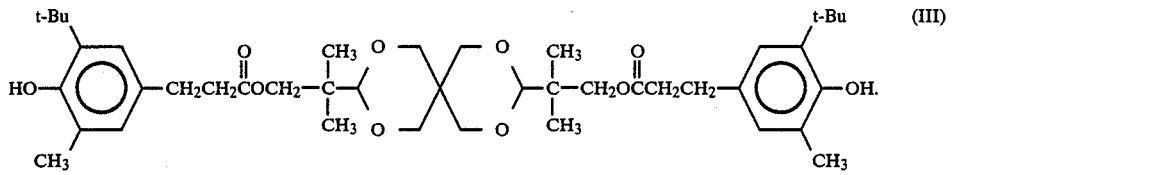

It is well known that the hydroxyphenylpropionic acid ester represented by the structural formula (III) can effectively be used to prevent various kinds of synthetic resin from deterioration such as softening, embrittlement, surface crack, discoloration, etc. caused by the action of heat, light and oxygen at the time of processing and use [Japanese Patent Application Kokai (Laid-open) Nos. 25826/84 and 231089/84]. As such synthetic resins, there may be mentioned polyolefins such as polyethylene, polypropylene, etc., styrene series synthetic resins such as polystyrene, impact-resistant polystyrene, ABS, etc., engineering plastics such as polyacetal, polyamide, etc., and polyurethane.

Hitherto, nothing is directly known about a method for producing such hydroxyphenylpropionic acid ester represented by the structural formula (III), but, to produce 3,9-bis{2-[3-(3,5-di-tert-butyl-4-hydroxyphenyl)-propionyloxy]-1,1-dimethylethyl}-2,4,8,10-tetraoxaspiro[5.5]undecane similar to said ester (III) and represented by the structural formula (IV),

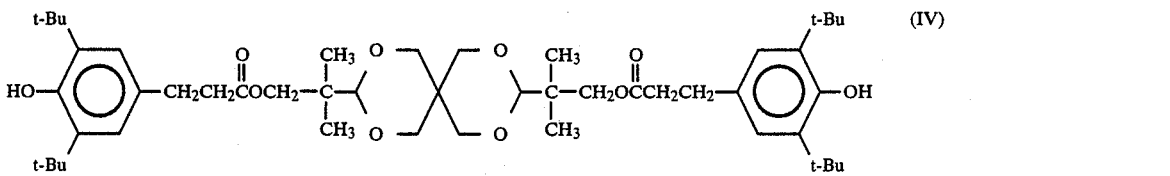

such a method is known that methyl 3-(3,5-di-tert-butyl-4-hydroxyphenyl)propionate and 3,9-bis(2-hydroxy-1,1-dimethylethyl)-2,4,8,10-tetraoxaspiro[5.5]undecane represented by the structural formula (II),

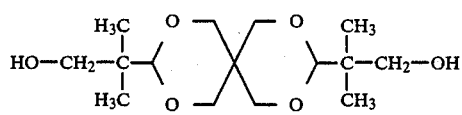

are ester-exchanged at 140°–150° C., under reduced pressure if necessary, using lithium amide as a catalyst [Japanese Patent Application Kokai (Laid-open) No. 25826/84].

However, when the compound represented by the structural formula (III), an object of the present invention, is produced by this method, the purity, color, etc. of the product obtained are not satisfactory, and in some cases, the product can not be even obtained. This method therefore is unsatisfactory as an industrial method.

Generally, in order to obtain a certain substance in good purity on a commercial scale, it is a common practice to purify the substance at the steps subsequent to the prescribed chemical reaction, making use of differences in physical properties between said substance and the impurities, although it is of course not necessary to conduct such purification if the substance already has a desired purity at the stage when it is obtained as a reaction product of said reaction. Specifically, methods such as recrystallization, distillation, adsorption, sublimation, etc. are used for such purification.

In the production of the desired hydroxyphenylpropionic acid ester represented by the structural formula (III), the product is generally low in purity, so that the subsequent purification is necessary. Since, however, said compound is very low in vapor pressure, distillation or sublimation is not suitable as a purification method. Purification by adsorption is an effective means, but in order that this method may succeed, the selectivity and amount of adsorbant are so important that the compound to be purified should be of considerably high purity. Purification by adsorption, therefore, cannot be used as an industrial purification method excet in those cases wherein economy is sacrified or impurities and colored products to be removed are luckily very small in amounts. Thus, the only remaining purification method for the hydroxyphenylpropionic acid ester represented by the structural formula (III) is recrystallization.

However, the hydroxyphenylpropionic acid ester represented by the structural formula (III) is a compound which is very difficult to crystallize, and it takes a glassy form at room temperature when obtained by the usual methods.

As a result of an extensive study, the present inventors have found that said ester of the structural formula (III) takes a certain crystalline form at room temperature. Thus, purification by recrystallization from solvent has come to be possible in principle. However, the present inventors have found at the same time that, in actual operation, impurities formed by the reaction disturb crystallization, so that the recrystallization is impossible unless the purity of said ester is previously raised to a very high level at the step of reaction.

However, when the ester exchange proposed in the foregoing Japanese Patent Application Kokai No. 25826/84 is applied using the catalyst and reaction condition described therein, it is impossible to obtain the product containing such a low amount of impurities as to make it possible to successfully apply the purification by recrystallization. The present inventors have made a further extensive study to solve these problems, and as a result, found that the product of excellent quality can be obtained simply and economically by carrying out the reaction at a particular temperature using a particular kind of catalyst. Based upon this finding the present invention has been accomplished.

An object of the present invention is to provide a method for producing 3,9-bis{2-[3-(3-tert-butyl-4-hydroxy-5-methylphenyl)-propionyloxy}-1,1-dimethylethyl}-2,4,8,10-tetraoxaspiro[5.5]undecane represented by the structural formula (III),

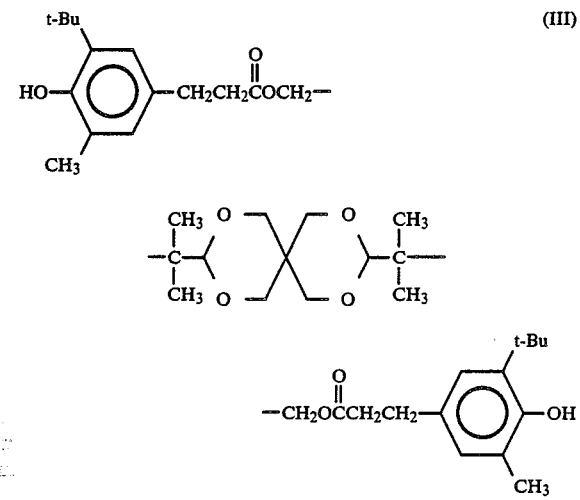

by the ester exchange of a 3-(3-tert-butyl-4-hydroxy-5-methylphenyl)-propionic acid ester represented by the general formula (I),

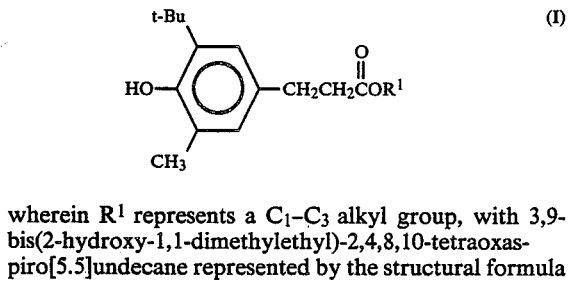

wherein $R^1$ represents a $C_1-C_3$ alkyl group, with 3,9-bis(2-hydroxy-1,1-dimethylethyl)-2,4,8,10-tetraoxaspiro[5.5]undecane represented by the structural formula (II),

characterized in that said ester exchange is carried out at a temperature of from 170° to 250° C. using an element belonging to the Group II of the periodic table or its compound as a catalyst.

In the general formula (I), $R^1$ includes methyl, ethyl, n-propyl and isopropyl groups. Specifically, said ester represented by the general formula (I) is the methyl, ethyl, n-propyl or isopropyl ester of 3-(3-tert-butyl-4-hydroxy-5-methylphenyl)propionic acid.

The amount of the ester of the general formula (I) is preferably in stoichiometrically a slight excess, i.e. about 2.1 to about 6 times by molar ratio based on the dihydric alcohol of the structural formula (II). Since, however, the ester exchange reaction itself is an equilibrium reaction, the reaction proceeds by removing an alcohol, $R^1OH$, resulting from the ester of the general formula (I). Therefore the amount of the ester is not critical. Further, in the present invention, the excess of the ester of the general formula (I) can easily be recovered by distillation in high yield and in high quality, there being little loss due to the use of excessive amount of the ester.

In the present invention, elements belonging to the Group II of the periodic table or their compounds are used as a catalyst for the ester exchange reaction. Specific examples thereof include beryllium, calcium, magnesium, the oxides, hydrides, hydroxides and carbonates of these elements, and the salts of these elements with organic acids (e.g. acetic acid, propionic acid). For example, there may be mentioned beryllium oxide, calcium, calcium oxide, calcium hydroxide, calcium hydride, calcium carbonate, calcium salts of organic acids (e.g. calcium acetate, calcium propionate), magnesium, magnesium oxide, etc. among which calcium oxide, calcium hydroxide and calcium hydride are particularly preferred. Of course, these catalysts can be used in combination, or together with other catalysts.

The amount of the catalyst is preferably 0.05 to 1.5 times by molar ratio based on the alcohol of the structural formula (II). When the amount is less than 0.05 time by mole, the reaction does not proceed substantially, while when it exceeds 1.5 times by mole, undesirable side reactions such as decomposition of the material and product are caused.

The reaction temperature is preferably from 170° to 250° C. When the temperature is lower than 170° C., the reaction does not proceed substantially, while when it exceeds 250° C., undesirable side reactions such as decomposition of the material and product are caused.

Generally, the reaction is carried out under atmospheric pressure. Of course, it may be carried out under reduced pressure in accordance with necessity. In order to expel the alcohol, $R^1OH$, resulting from the ester of the general formula (I) out of the system, it is possible to remove the alcohol by passing an inert gas (e.g. nitrogen, helium, argon, carbon dioxide, gaseous organic substances) through the system, or to distill the alcohol out of the system together with a solvent.

A reaction solvent may or may not be used. When it is used, solvents having a high boiling point and a high polarity such as N,N-dimethylformamide, dimethyl sulfoxide, sulfolane, N,N-dimethylacetamide, N-methylpyrrolidone, etc. are preferred.

The ester exchange reaction is continued until the alcohol, $R^1OH$, is not substantially formed from the ester of the general formula (I), and it is generally carried out for a period of time from 5 to 20 hours.

The reaction product obtained is after-treated by neutralization, washing with water, etc., and if necessary, the excess of the ester represented by the general formula (I), used as a material, is recovered.

According to the method of the present invention, the desired hydroxyphenylpropionic acid ester represented by the structural formula (III) occupies 94 to 98% of the reaction product thus obtained. Other substances present in the reaction product are 0 to 2% of the ester of the general formula (I) used as a material, 0 to 1% of an intermediate ester and a very small amount, as 1 to 2%, of other byproducts.

In contrast thereto, when the hydroxyphenylpropionic acid ester represented by the structural formula (III) is produced using the conventional catalyst and reaction temperature, the content of the desired ester of the structural formula (III) in the reaction product obtained is at best 90%, byproducts being present in as large an amount as 6 to 10% or more, and also said ester is of bad color and low quality. In addition, since the ester of the structural formula (III) is difficult to crystallize as described above, purification of the ester by recrystallization becomes substantially impossible because of such an increase in by-products. The conventional method is therefore completely unsatisfactory as a commercial-scale production method.

As described above, the method of the present invention is very advantageous to commercially produce the hydroxyphenylpropionic acid ester represented by the structural formula (III) with good purity, which was difficult to obtain on the commercial scale by the conventional method.

The present invention will be illustrated in more detail with reference to the following specific examples.

EXAMPLE 1

To a 500-ml four-necked flask equipped with a stirrer, a condenser, a thermometer and a nitrogen-introducing pipe were charged 200.3 g (0.8 mole) of methyl 3-(3-tert-butyl-4-hydroxy-5-methylphenyl)-propionate and 60.88 g (0.2 mole) of 3,9-bis(2-hydroxy-1,1-dimethylethyl)-2,4,8,10-tetraoxaspiro[5.5]undecane, and the mixture was heated at 150° C. for 30 minutes with stirring in nitrogen atmosphere to form a solution. After adding 2.25 g (0.04 mole) of calcium oxide to this solution, the solution was heated up to 190° C. and kept at the same temperature for 6 hours while distilling out formed methanol to complete the reaction. After completion of the reaction, the reaction solution was diluted with toluene, neutralized with aqueous dilute hydrochloric acid and washed with water. After removing toluene by evaporation, 97.1 g of methyl 3-(3-tert-butyl-4-hydroxy-5-methylphenyl)propionate, a material present in excess, was distilled off to obtain 148.3 g of a pale yellow highly viscous product. Analysis of this highly viscous product showed that said product contained 96.4% of 3,9-bis{2-[3-(3-tert-butyl-4-hydroxy-5-methylphenyl)-propionyloxy]-1,1-dimethylethyl}-2,4,8,10-tetraoxaspiro[5.5]undecane, the yield being 96.5% based on 3,9-bis(2-hydroxy-1,1-dimethylethyl)-2,4,8,10-tetraoxaspiro[5.5]undecane. The highly viscous product also contained methyl 3-(3-tert-butyl-4-hydroxy-5-methylphenyl)propionate which was a starting material and other by-products in the amounts of 1.2% and 2.4%, respectively.

EXAMPLES 2 AND 3

Procedure was repeated in the same manner as in Example 1 except that calcium oxide was replaced by each of 2.97 g (0.04 mole) of calcium hydroxide (Example 2) or 1.69 g (0.04 mole) of calcium hydride (Example 3). The results are shown in Table 1.

COMPARATIVE EXAMPLES 1 AND 2

Procedure was repeated in the same manner as in Example 1 except that calcium oxide was replaced by each of 2.25 g (0.02 mole) of potassium tert-butoxide (Comparative example 1) or 0.46 g (0.02 mole) of lithium amide (Comparative example 2), and that the reaction was completed at 150° C. under a pressure of 5 mmHg. The results are shown in Table 1.

COMPARATIVE EXAMPLES 3 AND 4

Procedure was repeated in the same manner as in Example 1 except that the temperature at which the reaction was completed was changed to 160° C. (Comparative example 3) or 260° C. (Comparative example 4). The results are shown in Table 1.

COMPARATIVE EXAMPLES 5 AND 6

Procedure was repeated in the same manner as in Example 1 except that the amount of calcium oxide was changed to 0.45 g (0.008 mole) (Comparative example 5) or 17.95 g (0.32 mole) (Comparative example 6). The results are shown in Table 1.

COMPARATIVE EXAMPLE 7

Procedure was repeated in the same manner as in Example 1 except that methyl 3-(3-tert-butyl-4-hydroxy-5-methylphenyl)propionate was replaced by 234 g (0.8 mole) of methyl 3-(3,5-di-tert-butyl-4-hydroxyphenyl)propionate. The result is shown in Table 1.

EXAMPLE 4

Fifty grams of the highly viscous product obtained in Example 1, 150 g of cyclohexane and 2.5 g of ethyl acetate were stirred to form a solution while heating at 70° C. for 1 hour. After rapidly cooling the resulting uniform solution to 30° C., 0.1 g of a seed crystal was added, and the solution was stirred at the same temperature for further 7 hours for crystallization. The formed crystals were filtered off, washed with cyclohexane and dried to obtain 46.4 g of white crystals having a melting point of 103°–107° C. Analysis of the white crystals showed that said crystals contained 98.6% of the desired 3,9-bis{2-[3-(3-tert-butyl-4-hydroxy-5-methylphenyl)propionyloxy]-1,1-dimethylethyl}-2,4,8,10-tetraoxaspiro[5.5]-undecane and 1.4% of by-products, and that the crystals contained no methyl 3-(3-tert-butyl-4-hydroxy-5-methylphenyl)propionate which was used as a starting material.

COMPARATIVE EXAMPLES 8 TO 13

Recrystallization was repeated in the same manner as in Example 4 except that 50 g of each of the highly viscous products obtained in Comparative examples 1 to 6 was used. The results are shown in Table 2.

TABLE 1

| | Kind of catalyst | Amount of catalyst (molar ratio)*1 | Temperature for completion of reaction (°C.) | Reaction time (hr) | Purity (wt. %) | | | | Yield of desired product (%)*1 |
|---|---|---|---|---|---|---|---|---|---|
| | | | | | Desired product*2 | Material*3 | Intermediate*4 | Others | |
| Example | | | | | | | | | |
| 1 | CaO | 0.2 | 190 | 6 | 96.4 | 1.2 | 0.8 | 1.6 | 96.5 |
| 2 | Ca(OH)$_2$ | 0.2 | 190 | 6 | 94.3 | 2.6 | 1.2 | 1.9 | 93.2 |
| 3 | CaH$_2$ | 0.2 | 190 | 6 | 96.1 | 1.6 | 0.7 | 1.6 | 96.0 |

TABLE 1-continued

| | Kind of catalyst | Amount of catalyst (molar ratio)*1 | Temperature for completion of reaction (°C.) | Reaction time (hr) | Purity (wt. %) | | | | Yield of desired product (%)*1 |
|---|---|---|---|---|---|---|---|---|---|
| | | | | | Desired product*2 | Material*3 | Intermediate*4 | Others | |
| Comparative example | | | | | | | | | |
| 1 | KOBu—t | 0.1 | 150 | 6 | 87.5 | 1.4 | 0.7 | 10.4 | 85.8 |
| 2 | LiNH2 | 0.1 | 150 | 6 | 88.9 | 1.5 | 0.8 | 8.8 | 87.5 |
| 3 | CaO | 0.2 | 160 | 12 | 52.4 | 1.2 | 45.2 | 1.2 | 40.1 |
| 4 | CaO | 0.2 | 260 | 6 | 91.5 | 0.5 | 1.1 | 6.9 | 88.5 |
| 5 | CaO | 0.04 | 190 | 24 | 65.9 | 0.9 | 32.3 | 0.9 | 56.3 |
| 6 | CaO | 1.6 | 190 | 6 | 94.2 | 1.3 | 0.7 | 3.8 | 93.5 |
| 7 | CaO | 0.2 | 190 | 10 | 90.5*5 | 4.4*6 | 3.5*7 | 1.6 | 85.2 |

*1Based on 3,9-bis(2-hydroxy-1,1-dimethylethyl)-2,4,8,10-tetraoxaspiro[5.5]undecane
*23,9-Bis{2-[3-(3-tert-butyl-4-hydroxy-5-methylphenyl)propionyloxy]-1,1-dimethylethyl}-2,4,8,10-tetraoxaspiro[5.5]undecane
*3Methyl 3-(3-tert-butyl-4-hydroxy-5-methylphenyl)propionate
*43-{2-[3-(3-Tert-butyl-4-hydroxy-5-methylphenyl)propionyloxy]-1,1-dimethylethyl}-9-(2-hydroxy-1,1-dimethylethyl)-2,4,8,10-tetraoxaspiro[5.5]undecane
*53,9-Bis{2-[3-(3,5-di-tert-butyl-4-hydroxyphenyl)propionyloxy]-1,1-dimethylethyl}-2,4,8,10-tetraoxaspiro[5.5]undecane
*6Methyl 3-(3,5-di-tert-butyl-4-hydroxyphenyl)propionate
*73-{2-[3-(3,5-Di-tert-butyl-4-hydroxyphenyl)propionyloxy]-1,1-dimethylethyl}-9-(2-hydroxy-1,1-dimethylethyl)-2,4,8,10-tetraoxaspiro[5.5]undecane

TABLE 2

| | Weight of crystal (g) | Purity of desired product (wt. %) | Time required for crystallization (hr) | Melting point (°C.) |
|---|---|---|---|---|
| Example 4 | 46.4 | 98.6 | 7 | 103–107 |
| Comparative example | | | | |
| 8 | 32.2 | 94.2 | 24 | 92–98 |
| 9 | 35.3 | 93.9 | 24 | 90–98 |
| 10 | 0* | | 144* | |
| 11 | 42.5 | 96.2 | 12 | 95–100 |
| 12 | 0* | | 144* | |
| 13 | 43.8 | 96.8 | 12 | 97–101 |

*Did not crystallize.

What is claimed is:

1. A method for producing 3,9-bis{2-[3-(3-tert-butyl-4-hydroxy-5-methylphenyl)propionyloxy]-1,1-dimethylethyl}-2,4,8,10-tetraoxaspiro[5.5]undecane represented by the formula (III),

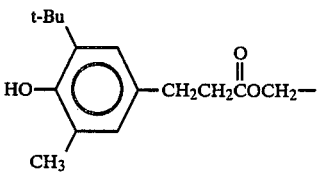

(III)

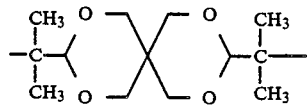

which comprises reacting, by an ester exchange reaction, a 3-(3-tert-butyl-4-hydroxy-5-methylphenyl)-propionic acid ester represented by the formula (I), $$\underset{\underset{CH_3}{\big|}}{\overset{\underset{t\text{-}Bu}{\big|}}{HO-\bigcirc-CH_2CH_2COR^1}} \quad (I)$$

wherein $R^1$ represents a $C_1$–$C_3$ alkyl group, with 3,9-bis(2-hydroxy-1,1-dimethylethyl)-2,4,8,10-tetraoxaspiro[5.5]-undecane represented by the formula (II), $$HO-CH_2-\underset{\underset{H_3C}{\big|}}{\overset{\underset{H_3C}{\big|}}{C}}\diagup\!\!\!\diagdown\underset{\underset{CH_3}{\big|}}{\overset{\underset{CH_3}{\big|}}{C}}-CH_2-OH$$

in which said ester exchange reaction is carried out at a temperature of from 170° to 250° C. using a calcium compound as a catalyst in an amount of 0.05–1.5 times, by molar ratio, the amount of the compound of formula (II).

2. A method as claimed in claim 1, wherein the catalyst is calcium oxide.

3. A method as claimed in claim 1, wherein the catalyst is calcium hydride.

4. A method as claimed in claim 1, wherein the catalyst is calcium hydroxide.